United States Patent
Wegener

(10) Patent No.: US 10,329,530 B2
(45) Date of Patent: Jun. 25, 2019

(54) CELL WASHING SYSTEM AND METHODS FOR WASHING SMALL VOLUMES OF CELLS

(71) Applicant: Fenwal, Inc., Lake Zurich, IL (US)

(72) Inventor: Christopher J. Wegener, Libertyville, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 15/399,842

(22) Filed: Jan. 6, 2017

(65) Prior Publication Data

US 2017/0204371 A1 Jul. 20, 2017

Related U.S. Application Data

(60) Provisional application No. 62/279,886, filed on Jan. 18, 2016.

(51) Int. Cl.
| | |
|---|---|
| *C12N 5/078* | (2010.01) |
| *C12N 5/00* | (2006.01) |
| *B01L 3/00* | (2006.01) |
| *C12Q 3/00* | (2006.01) |
| *A61M 1/02* | (2006.01) |
| *A61M 1/26* | (2006.01) |
| *A61M 1/36* | (2006.01) |

(52) U.S. Cl.
CPC .......... *C12N 5/0634* (2013.01); *A61M 1/0272* (2013.01); *A61M 1/0281* (2013.01); *A61M 1/262* (2014.02); *A61M 1/3692* (2014.02); *B01L 3/502* (2013.01); *C12N 5/0081* (2013.01); *C12Q 3/00* (2013.01); *A61M 2205/123* (2013.01); *A61M 2205/128* (2013.01); *B01L 2200/026* (2013.01); *B01L 2300/0681* (2013.01); *B01L 2400/0409* (2013.01); *B01L 2400/0478* (2013.01)

(58) Field of Classification Search
CPC ..... C12N 5/0634; C12N 5/0081; B01L 3/502; C12Q 3/00
USPC .......................................... 422/535
See application file for complete search history.

(56) References Cited

U.S. PATENT DOCUMENTS

| | | | |
|---|---|---|---|
| 5,053,121 | A | 10/1991 | Schoendorfer et al. |
| 5,462,416 | A | 10/1995 | Dennehey et al. |
| 5,928,214 | A | 7/1999 | Rubinstein et al. |

(Continued)

OTHER PUBLICATIONS

European Patent Office, European Search Report, counterpart EP Appl. No. 17151988, dated Jun. 16, 2017.

*Primary Examiner* — Jill A Warden
*Assistant Examiner* — Jacqueline Brazin
(74) *Attorney, Agent, or Firm* — Cook Alex Ltd.

(57) ABSTRACT

A fluid circuit for cell washing is provided that comprises a spinning membrane separator and a fluid management system comprising a cassette that defines the fluid pathways, and including internally mechanical valving, pressure sensing and air sensing for controlling flow through the fluid pathways, thus minimizing the volume of the fluid circuit. Additionally, the fluid circuit comprises syringes that are acted on by syringe pumps associated with the hardware component of the system to provide pressure for moving fluid through the circuit. Preferably, the syringes are connected directly to the cassette, or formed integrally within the cassette housing, thus further minimizing the volume of the fluid circuit.

17 Claims, 18 Drawing Sheets

(56) References Cited

U.S. PATENT DOCUMENTS

| | | |
|---|---|---|
| 6,491,678 B1 | 12/2002 | Rubinstein et al. |
| 6,582,349 B1 | 6/2003 | Cantu et al. |
| 7,011,852 B2 | 3/2006 | Sukavaneshvar et al. |
| 7,179,391 B2 | 2/2007 | Leach et al. |
| 7,364,657 B2 | 4/2008 | Mandrusov et al. |
| 7,780,860 B2 | 8/2010 | Higgins et al. |
| 7,832,566 B2 | 11/2010 | Leach et al. |
| 7,914,689 B2 | 3/2011 | Higgins et al. |
| 7,954,646 B2 | 6/2011 | Leach et al. |
| 8,048,321 B2 | 11/2011 | Leach et al. |
| 8,163,184 B2 | 4/2012 | Leach et al. |
| 8,439,889 B2 | 5/2013 | Sano |
| 8,961,787 B2 | 2/2015 | Wood et al. |
| 8,968,991 B2 | 3/2015 | Mandrusov et al. |
| 9,452,254 B2 | 9/2016 | Kimura et al. |
| 9,603,986 B2 | 3/2017 | Kusters et al. |
| 9,709,549 B2 | 7/2017 | Wood et al. |
| 9,717,842 B2 | 8/2017 | Min et al. |
| 9,744,498 B2 | 8/2017 | Wegener |
| 2002/0128583 A1* | 9/2002 | Min .................. A61M 1/3679 604/6.01 |
| 2013/0092630 A1 | 4/2013 | Wegener |
| 2013/0273548 A1* | 10/2013 | Mastromatteo ......... B01L 3/502 435/6.12 |
| 2013/0341291 A1 | 12/2013 | Wegener et al. |
| 2014/0077488 A1 | 3/2014 | Wegener et al. |
| 2014/0199680 A1 | 7/2014 | Min et al. |
| 2015/0060363 A1 | 3/2015 | Kusters et al. |
| 2015/0079194 A1* | 3/2015 | Hanna ............... A61K 38/1722 424/530 |
| 2015/0216563 A1 | 8/2015 | Mandrusov et al. |
| 2016/0177262 A1 | 6/2016 | Wegener et al. |
| 2017/0007758 A1 | 1/2017 | Kimura et al. |
| 2017/0274134 A1 | 9/2017 | Min et al. |
| 2018/0015418 A1 | 1/2018 | Binninger et al. |

\* cited by examiner

CELL WASHING SYSTEM AND METHODS FOR WASHING SMALL VOLUMES OF CELLS

TECHNICAL FIELD

The present disclosure is directed to systems and methods for washing suspensions of biological cells. More particularly, the present disclosure is directed to systems and methods for washing small volumes of biological cells.

BACKGROUND

A number of well-known therapies are currently practiced in which a targeted cellular blood component (e.g., red blood cells, white blood cells, and platelets) is separated from whole blood and stored for later infusion to a patient. The targeted cellular product (e.g., red blood cells or platelets) may be in a suspension that includes plasma and/or some other supernatant. As such, it is sometimes desirable to "wash" the cellular suspension (typically with saline) to remove the plasma/supernatant, as well as any non-target cellular material, prior to reinfusion.

Systems and methods for cell washing are exemplified by US 2013/0341291, US 2013/0092630, and US 2014/0199680, each of which is incorporated herein by reference. Each of these published applications discloses cell washing methods utilizing systems and fluid circuits including a spinning membrane separator. Such systems include peristaltic pumps and pinch valves that act on tubing to direct flow within the fluid circuit.

The fluid circuits in the cited published applications have a relatively large internal volume, and thus require relatively large volumes of wash or flush media to clear processed fluid through the fluid circuit. While such systems and fluid circuits are capable of washing and reducing the volume of the targeted cellular component into final volumes of ranging from approximately 50 mL to 5,000 mL, there are instances in which smaller final volumes (e.g., 10 mL) are desired, such as when processing single-dose quantities of mononuclear cell products. Thus, it would be desirable to provide systems and methods for washing small volumes of cellular suspensions.

SUMMARY

In a first aspect of the disclosure, a fluid circuit for cell washing is provided that comprises a spinning membrane separator and a fluid management system comprising a cassette that defines the fluid pathways, and including internal mechanical valving and sensors (for sensing, e.g., pressure, air, fluid interfaces, etc.) for controlling flow through the fluid pathways, thus minimizing the volume of the fluid circuit by minimizing the tubing required. Additionally, the fluid circuit comprises syringes that are acted on by syringe pumps associated with the hardware component of the system to provide pressure for moving fluid through the circuit. Preferably, the syringes are connected directly to the cassette, or the barrels of the syringes may be integrally formed with the cassette, thus further minimizing the volume of the fluid circuit.

In a second aspect, a disposable kit for washing a suspension of cellular material is provided comprising a spinning membrane separator having an inlet for flowing the suspension of cellular material to be washed and a wash medium into the spinning membrane separator, a first outlet for flowing retentate comprising target components from the spinning membrane separator, and a second outlet for flowing filtrate comprising non-target components of the cellular suspension (including supernatant) and wash medium from the spinning membrane separator. The kit further includes containers for receiving the retentate and the filtrate, and also either includes a container of wash medium integrally connected to the kit or is configured to be connected to a container of wash medium. Alternatively, a sterile vent can replace each of the containers for receiving the retentate and the filtrate. Optionally, the kit may also include either a container of diluent integrally connected to the kit or is configured to be connected to a container of diluent.

Fluid management of the kit is controlled by a flow control cassette comprising a housing and having a first fluid pathway with a first inlet configured to be in fluid communication with a source of the suspension of cellular material to be washed, a second inlet configured to be in fluid communication with the container of wash medium, and an outlet in fluid communication with the inlet of the spinning membrane separator; a second fluid pathway with an inlet in fluid communication with the first outlet of the spinning membrane separator for flowing retentate, a first outlet in fluid communication with the container for receiving the retentate, and a second outlet in fluid communication with a first syringe; a third fluid pathway with an inlet in fluid communication with the second outlet of the spinning membrane separator for flowing filtrate, a first outlet in fluid communication with the container for receiving the filtrate, and a second outlet in fluid communication with a second syringe; at least one device for selectively occluding the fluid pathways associated with each of the first, second and third fluid pathways; and at least one fluid interface detector associated with each of the first, second and third fluid pathways. Preferably, a device for selectively occluding is associated with each of the first inlet and second inlet of the first fluid pathway, the inlet and first outlet of the second fluid flow pathway, and the inlet and first outlet of the third fluid pathway. Optionally, the second fluid pathway may include a second inlet configured to be in fluid communication with a source of diluent, and a device for selectively occluding is associated with the second inlet.

In a third aspect, each of the first and second syringe comprises a plunger and a body or barrel having a discharge port, each syringe being removably secured directly to the housing of the cassette by the discharge port.

In a fourth aspect, a method for washing a suspension of cellular material is provided. The method includes priming various portions of the disposable kit with wash media, loading the spinning membrane separator with a volume of the suspension of cells to be washed, removing the supernatant and non-target materials from the separator, washing the components remaining in the separator, and removing or clearing the washed components from the separator.

More particularly, the disposable kit may be primed with wash media by withdrawing the plunger of the first syringe while occluding the first fluid pathway adjacent its first inlet, the second fluid pathway adjacent its first outlet, and the third fluid pathway adjacent its inlet to draw wash media into the first fluid pathway; at least partially depressing the plunger of the first syringe while opening the first fluid pathway adjacent its first outlet and occluding the first fluid pathway adjacent its second inlet to prime the first fluid pathway up to the source of the suspension of cellular material to be washed; and further depressing the plunger of the first syringe while opening the second fluid pathway adjacent its first outlet and occluding the first fluid pathway adjacent its inlet to vent air to the container for receiving retentate.

Alternatively, to further reduce the volume of wash media, the disposable kit may be primed with wash media by drawing wash media from its source only up to the inlet to the first fluid pathway.

The spinning membrane separator is then loaded with a volume of the suspension of cellular material to be washed by withdrawing the plunger of the first syringe while opening the first fluid pathway adjacent its first inlet and occluding the first fluid pathway adjacent its second inlet, opening the second fluid pathway adjacent its inlet and occluding the second fluid flow path adjacent its first outlet; and occluding the third fluid pathway adjacent its inlet to draw the volume of suspension into the separator; and depressing the plunger of the first syringe while opening the second fluid pathway adjacent its first outlet and occluding the first fluid pathway adjacent its inlet to vent air either to the container for receiving retentate or to the vent filter.

The volume of the suspension of cells in the separator is then washed by withdrawing the plunger of the second syringe while opening the first fluid pathway adjacent its first inlet and occluding the first fluid pathway adjacent its second inlet, occluding the second fluid pathway adjacent inlet, and opening the third fluid path way adjacent its inlet and occluding the third fluid flow path adjacent its first outlet to simultaneously draw additional suspension into the separator and supernatant into the second syringe; further withdrawing the plunger of the second syringe while occluding the first fluid pathway adjacent its first inlet and opening the first fluid pathway adjacent its second inlet, occluding the second fluid pathway adjacent its inlet, and occluding the third fluid pathway adjacent its first outlet to draw wash media into and through the spinning membrane separator and into the second syringe.

The spinning membrane separator is then cleared of washed cells by occluding the third fluid pathway adjacent its inlet and opening the third fluid pathway adjacent its first outlet while depressing the plunger of the second syringe to flow supernatant and wash media into the container for filtrate, and opening the second fluid pathway adjacent its inlet and occluding the second fluid pathway adjacent its first outlet, occluding the first fluid pathway adjacent its first inlet and opening the first fluid pathway adjacent its second inlet while withdrawing the plunger of the first syringe to draw washed cellular matter into the first syringe.

Washed cellular material may then be flowed from the first syringe to the container for receiving retentate by depressing the plunger of the first syringe while occluding the second fluid pathway adjacent its inlet and opening the second fluid pathway adjacent its first outlet. The steps of loading the spinning membrane separator, washing the volume of cells in the separator, and clearing the spinning membrane of washed cells are repeated until the source of the suspension of cellular material to be washed is emptied.

Optionally, after the washed cellular material is flowed into the container for receiving retentate, a diluent, such as a cryoprotectant, may be introduced into the collection container for the washed cellular material.

DETAILED DESCRIPTION

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Figure 1:
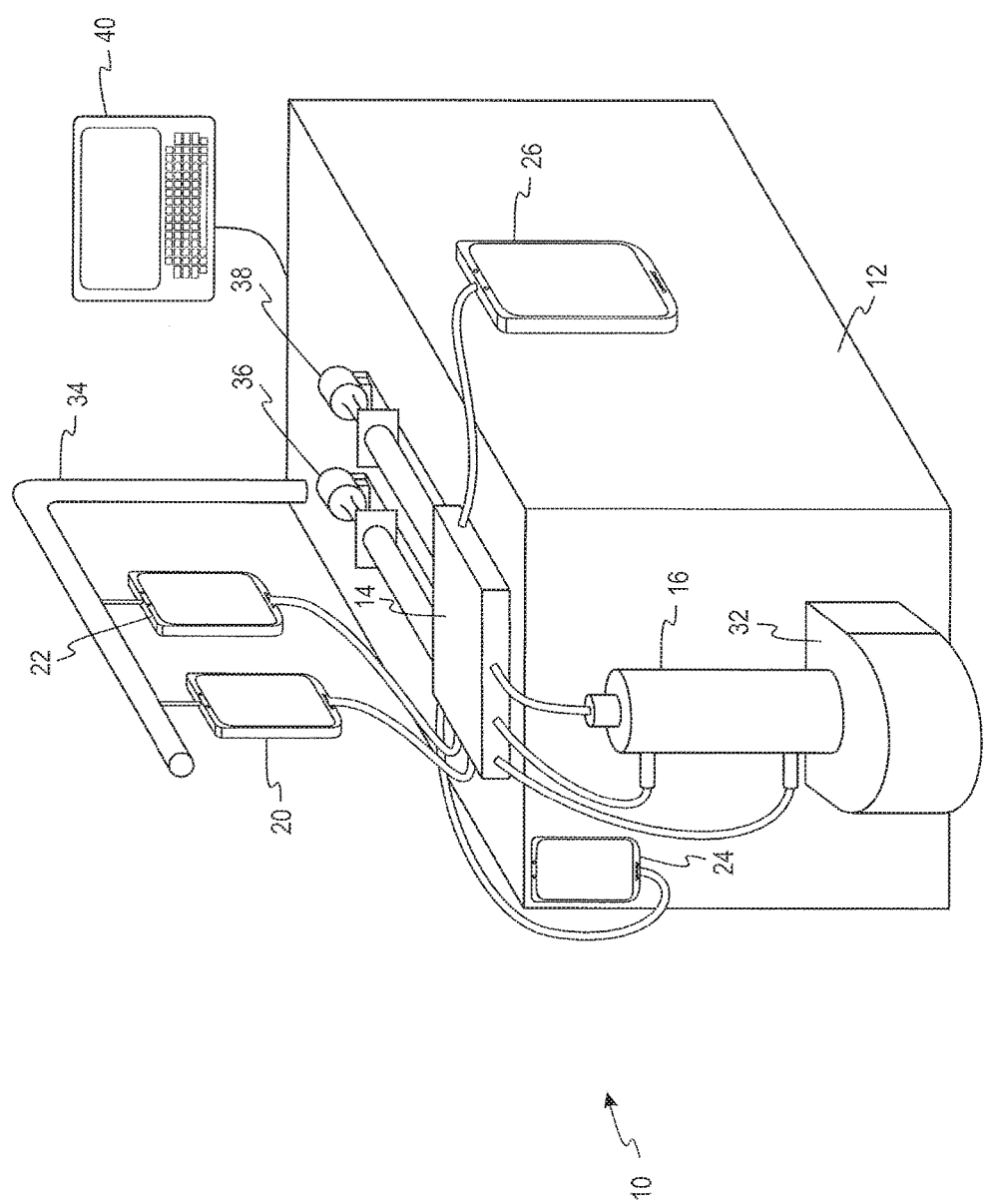
FIG. 1 is a perspective view of a system for washing small volumes of cellular suspensions in accordance with the present invention.
Figure 2:
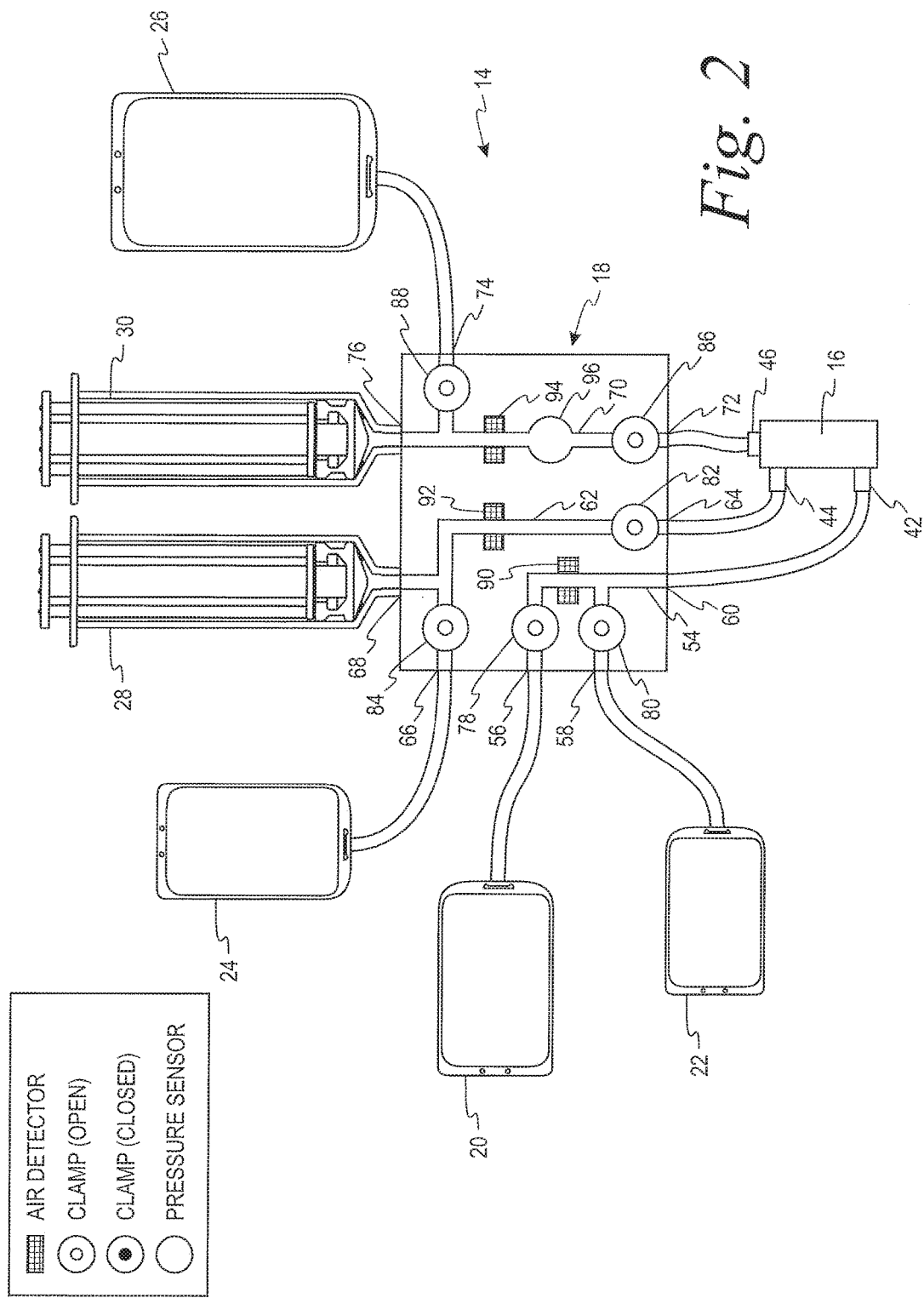
FIG. 2 is a schematic view of a disposable kit for use in the system of FIG. 1.

Turning to FIG. 1, there is seen a system 10 for cell washing in accordance with the present disclosure including a reusable hardware component 12 and a disposable kit component 14, best seen in FIG. 2.

The disposable kit 14 includes a spinning membrane separator 16, such as is well known in the art, a cassette 18, for providing fluid management through the kit, and various containers 20, 22, 24 and 26, and syringes 28 and 30, each comprising a body or barrel portion and a plunger, in fluid communication with the cassette, which are described in greater detail below. Tubings interconnect each of the various containers, as well as the inlet and outlets of the spinning membrane separator, to the cassette. Preferably the length of each of the interconnecting tubings is kept as short as possible to further minimize the internal volume of the kit. Also, it is preferable that discharge ports of the syringes be configured to be removably connected directly to the cassette, again to minimize the internal volume of the kit. Alternatively, the syringes and/or the spinning membrane separator may be integrally formed as part of the cassette, so as to be internal to the cassette housing, to further reduce the tubing volume associated with the kit.

The reusable hardware component 12 includes a drive system/support 32 for the spinning membrane separator 16, supports 34 for the various containers of the disposable kit, a syringe pump 36, 38 for each syringe 28, 30, and a programmable controller 40 for automatically controlling operation of the system.

Specifically, the disposable kit 14 comprises a spinning membrane separator 16 having an inlet 42 for flowing the suspension of cellular material to be washed and a wash medium into the spinning membrane separator, a first outlet 44 for flowing retentate comprising washed cells from the spinning membrane separator, and a second outlet 46 for flowing filtrate comprising a non-cellular component of the cellular suspension and wash medium from the spinning membrane separator.

Figure 3:
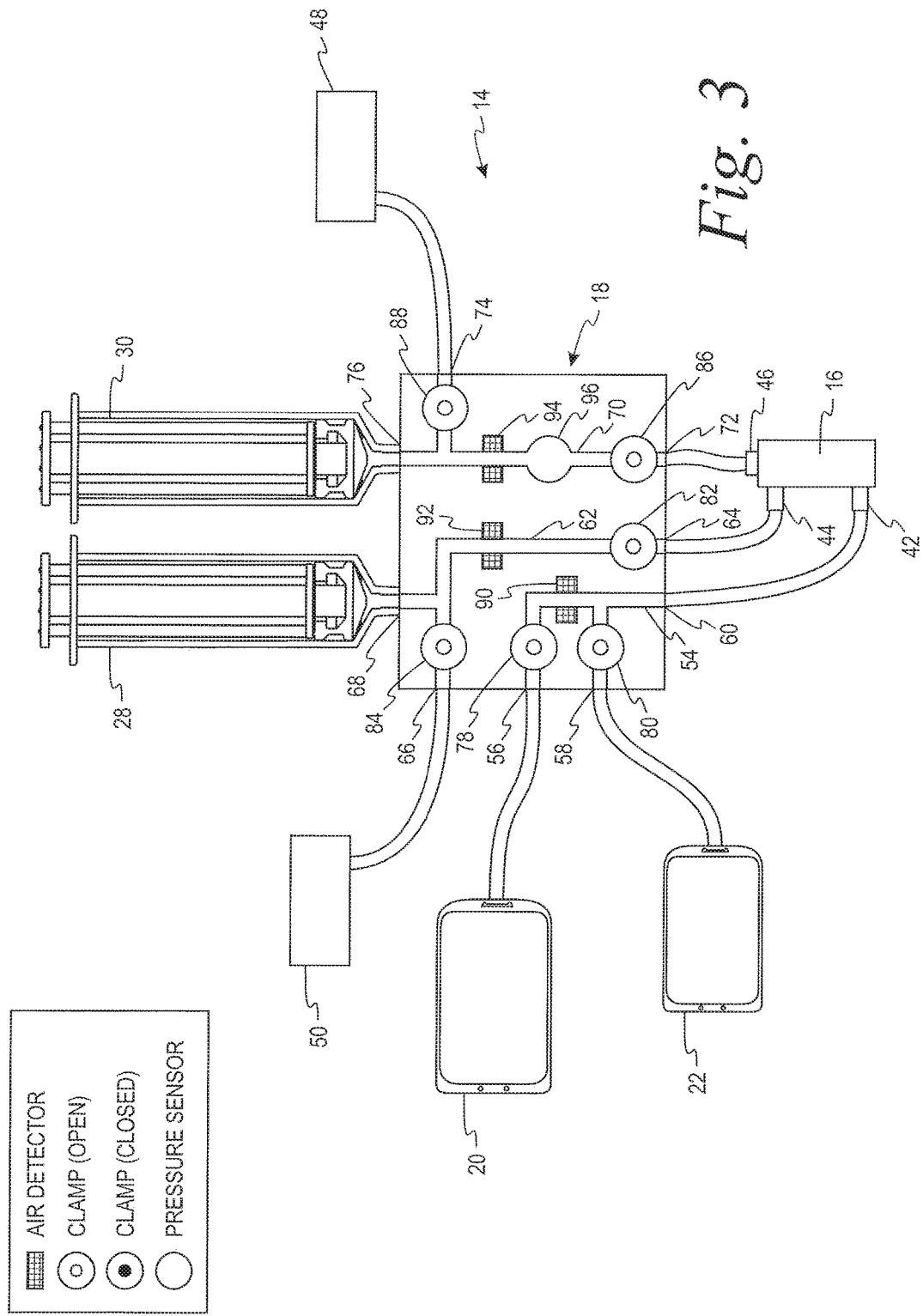
FIG. 3 is a schematic view of an alternate configuration of the disposable kit of FIG. 2.

The kit further includes containers 24, 26 for receiving the retentate and the filtrate, respectively, and also either includes a container 22 of wash medium integrally connected to the kit at the time of manufacture or is configured to be connected to a container of wash medium at the point of use. Alternatively, with reference to FIG. 3, a sterile vent 48, 50 can replace each of the containers 24, 26 for receiving the retentate and the filtrate.

Fluid management of the kit is controlled by the cassette 18. The cassette 18 comprises a housing 52 having a series of fluid pathways therein interconnecting the various other components of the disposable kit, each of the fluid pathways having flow control mechanisms, such as valves/clamps and air detectors/pressure sensors associated therewith that are automatically operated by the controller 40. By having the valves/clamps, detectors and sensors integral with the cassette, the lengths of the tubings interconnecting the various containers of the system to the cassette can be minimized, thus reducing the internal volume of the kit.

Specifically, the cassette 18 includes a first fluid pathway 54 with a first inlet 56 configured to be in fluid communication with container 20 of the suspension of cellular material to be washed. The first fluid pathway 54 further includes a second inlet 58 is in fluid communication with the container of wash media 20, and an outlet 60 in fluid communication with the inlet 42 of the spinning membrane separator 16.

The cassette 18 includes a second fluid pathway 62 having an inlet 64 in fluid communication with the first outlet 44 of the spinning membrane separator 16 for flowing the retentate. The second fluid pathway further includes a first outlet 66 in fluid communication with the container 24 for receiving the retentate, and a second outlet 68 in fluid communication with the first syringe 28.

A third fluid pathway 70 is provided that includes an inlet 72 in fluid communication with the second outlet 46 of the spinning membrane separator 16 for flowing filtrate. The third fluid pathway 70 further includes a first outlet 74 in fluid communication with the container 26 for receiving the filtrate, and a second outlet 76 in fluid communication with the second syringe 30.

Devices for selectively occluding the fluid pathways are associated with each of the first, second and third fluid pathways. Such occluding devices may take the form of valves or clamps. Preferably, a first such valve/clamp 78 is associated with the 56 first inlet of the first fluid pathway 54, a second valve/clamp 80 is associated with the second inlet 58 of the first fluid pathway 54, a third valve/clamp 82 is associated with the inlet 64 of the second fluid pathway 62, a fourth valve/clamp 84 is associated with the first outlet 66 of the second fluid flow pathway 62, a fifth valve/clamp 86 is associated with the inlet 72 of the third fluid pathway 70, and a sixth valve/clamp 88 is associated with the first outlet 74 of the third fluid pathway 70.

Each of the first, second and third fluid pathways is also provided with a sensor 90, 92, 94, respectively, that is able to detect differences in the fluid passing by. Specifically, the sensors 90, 92 and 94 are able to detect interfaces between different types of fluids, such as an air-liquid interface, a wash media-retentate interface, and a wash media-filtrate interface. Upon the detection of such interfaces, a signal is sent to the controller that will act to control the configuration of the valves/clamps (open or closed) and actuate the syringe pumps 36, 38 to move fluid through the kit in accordance with a cell washing procedure. The cassette 14 may also include a pressure sensor 96 for monitoring purposes.

Figure 4:
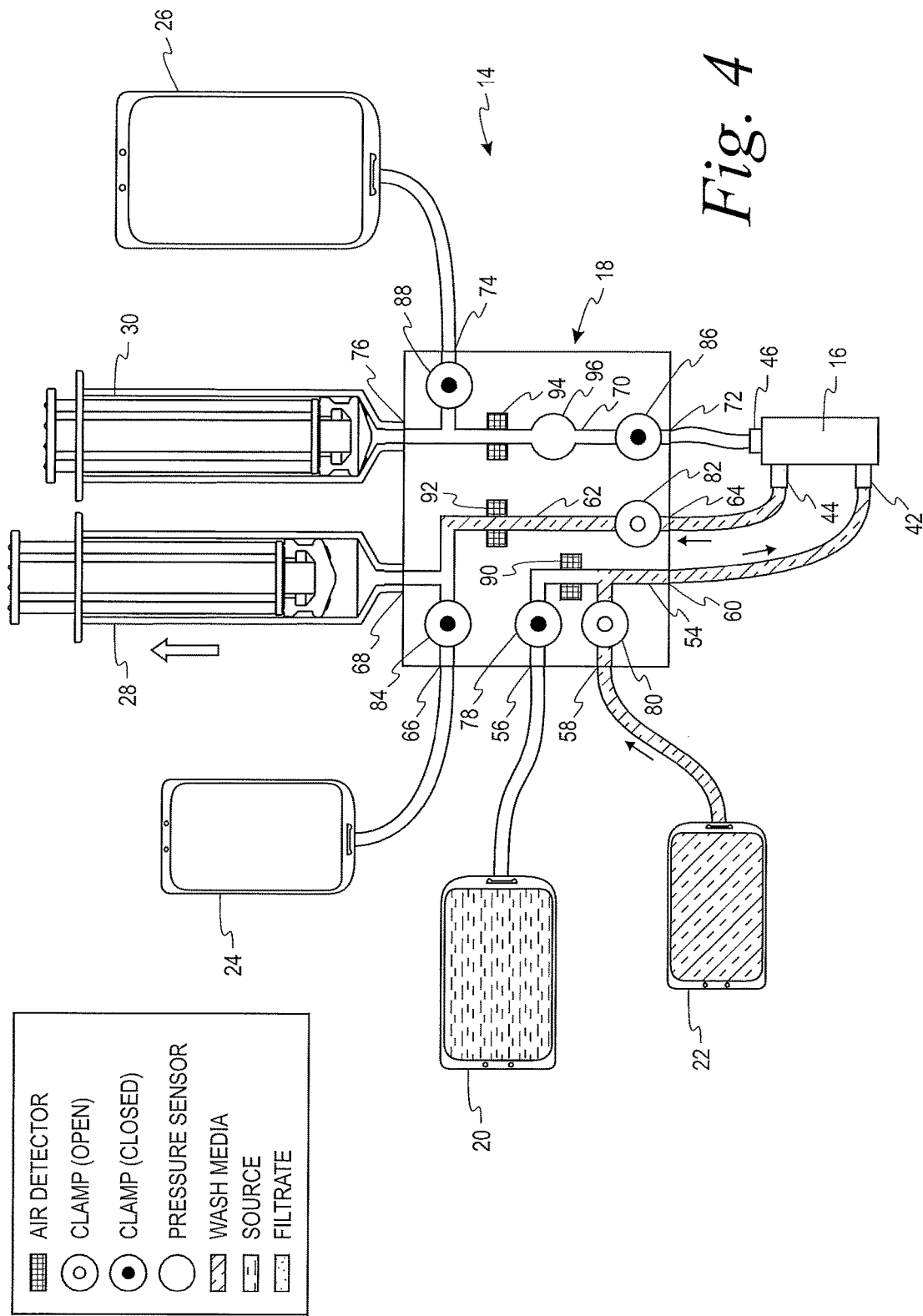
FIGS. 4-15 are schematic views of the disposable kit of FIG. 2 showing the configuration of the kit during the various stages of a cell washing procedure, with FIGS. 4-6 illustrating the prime phase of the procedure, FIGS. 7-11 illustrating the steps of the first wash phase, and FIGS. 12-15 illustrating the steps of a subsequent wash phase.
Figure 6:
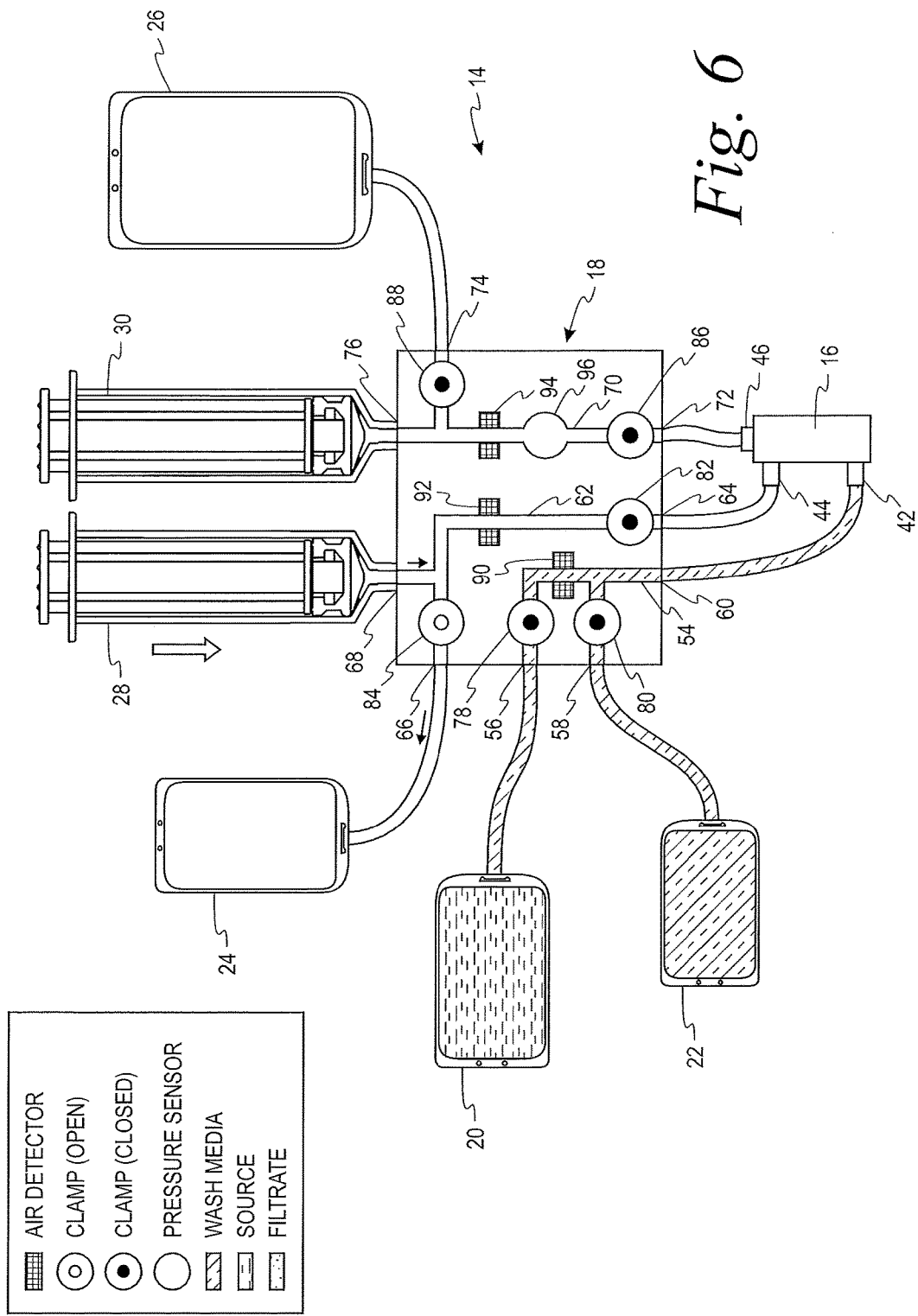
Figure 7:
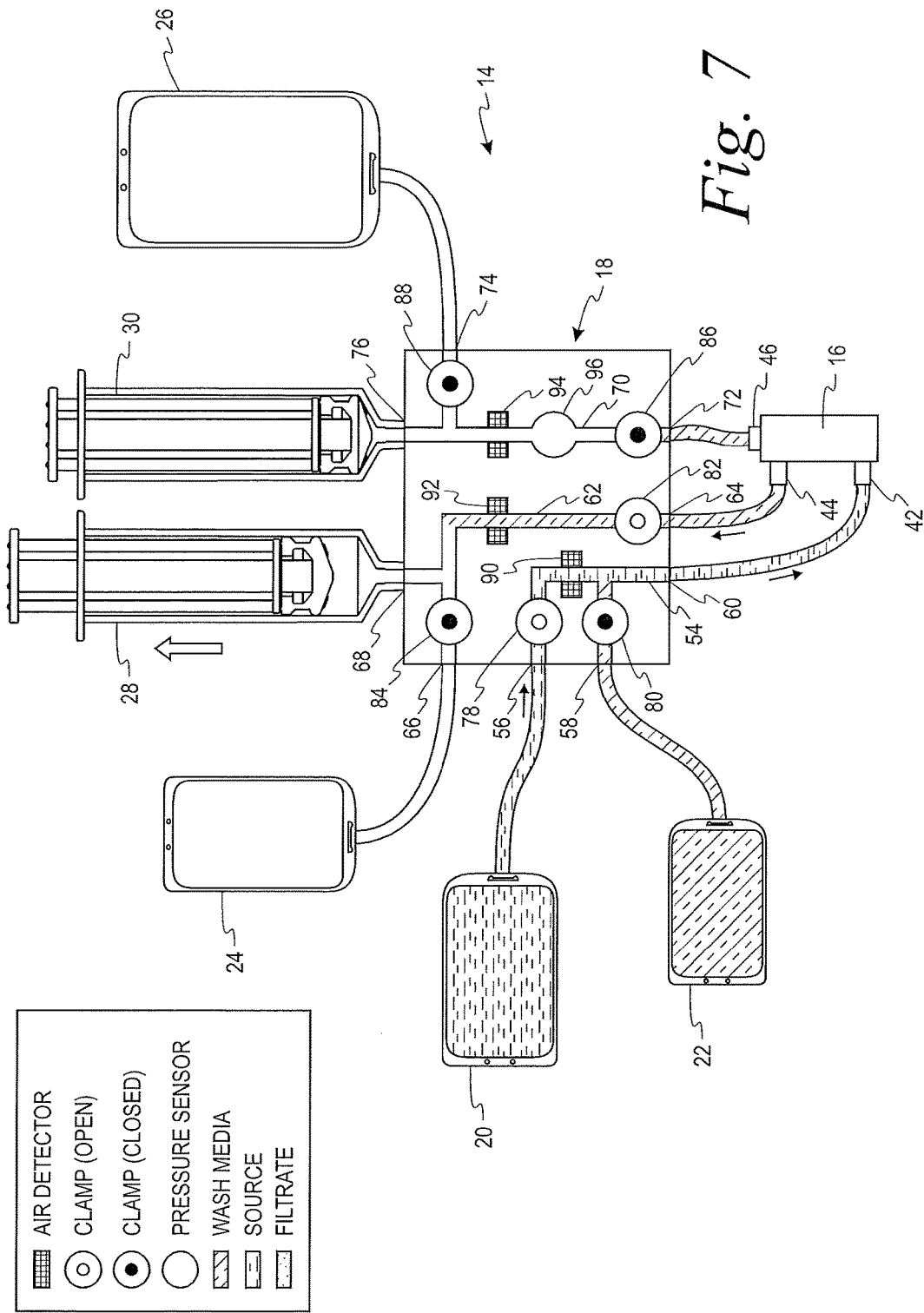
Figure 8:
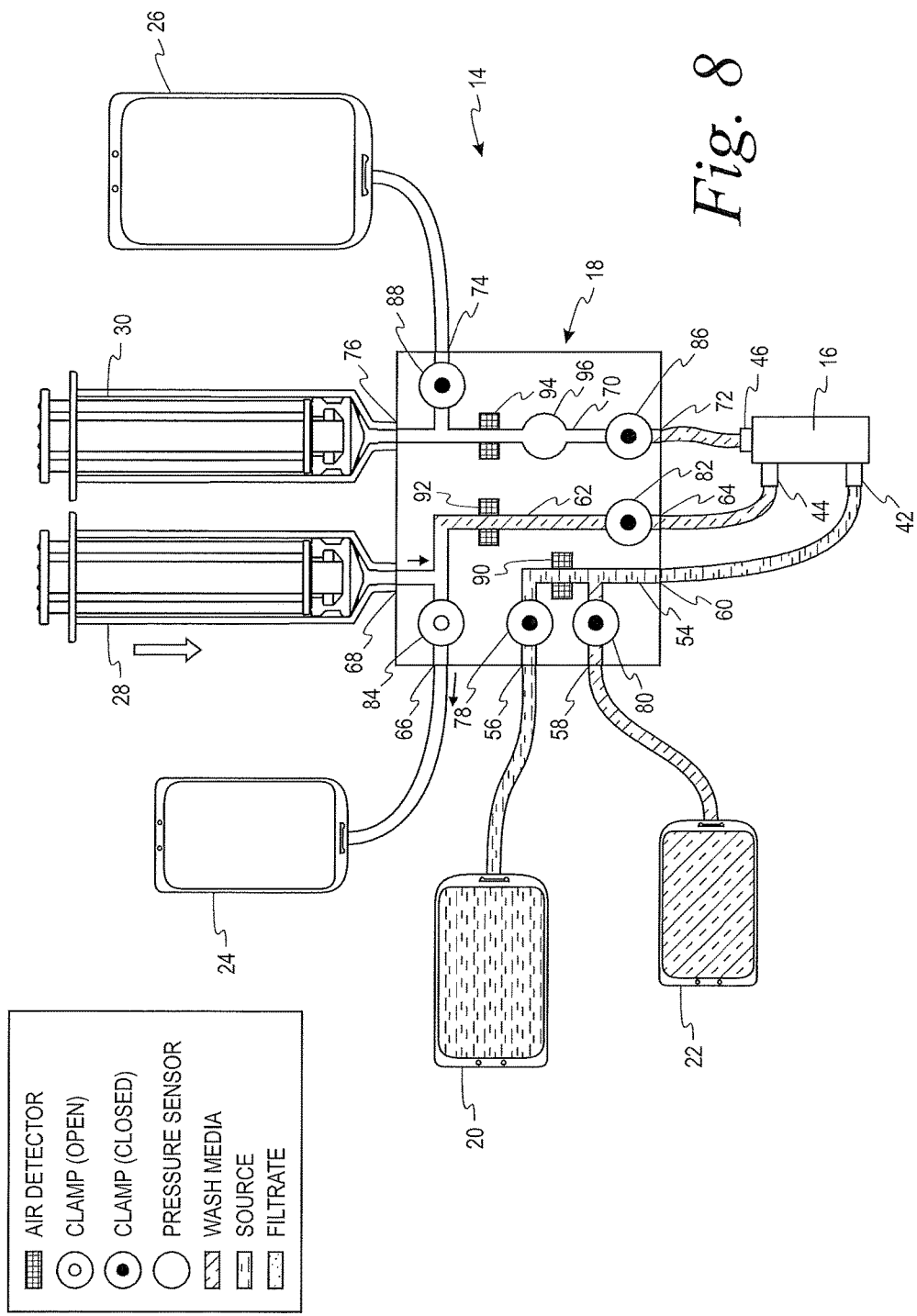
Figure 9:
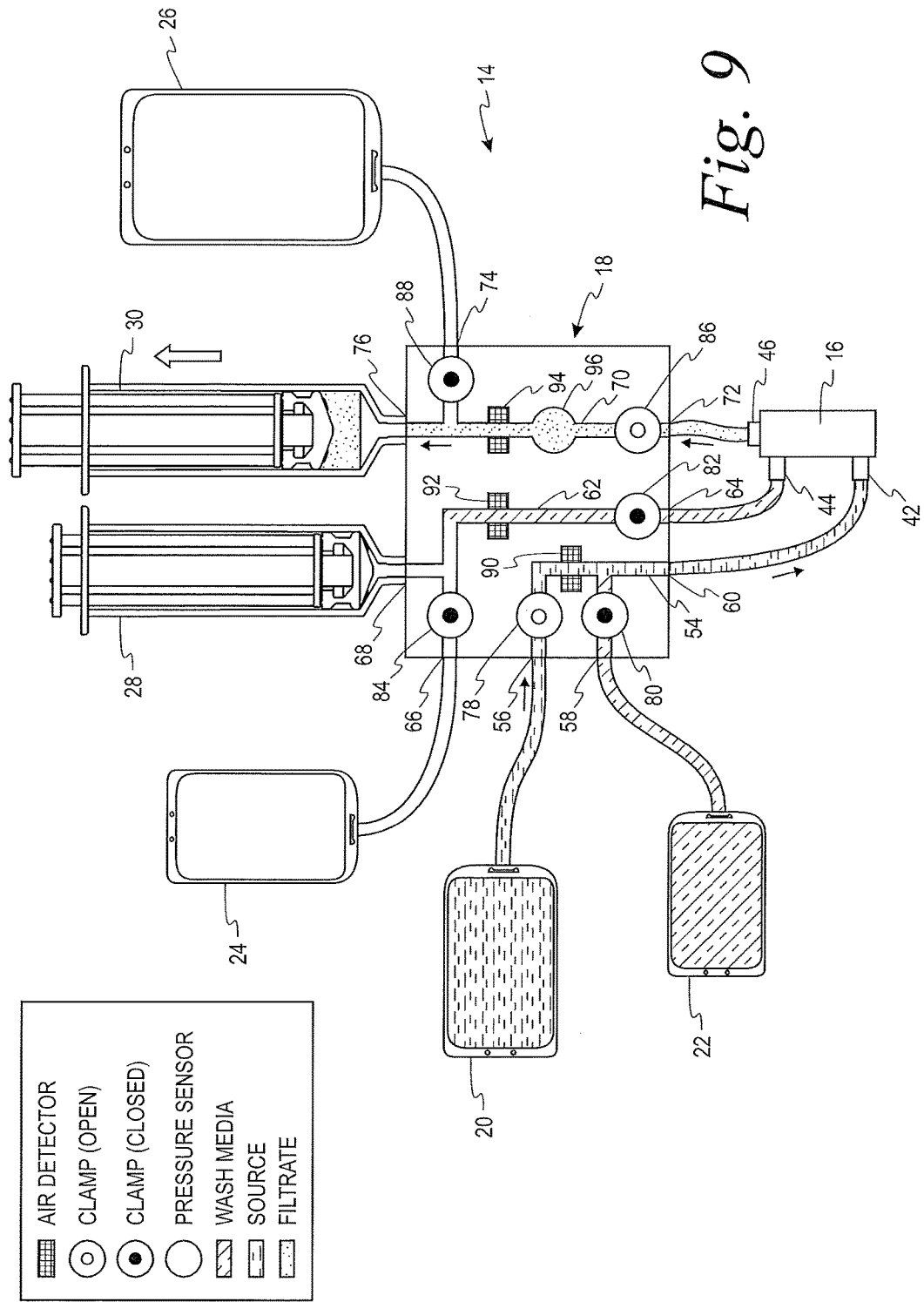
Figure 10:
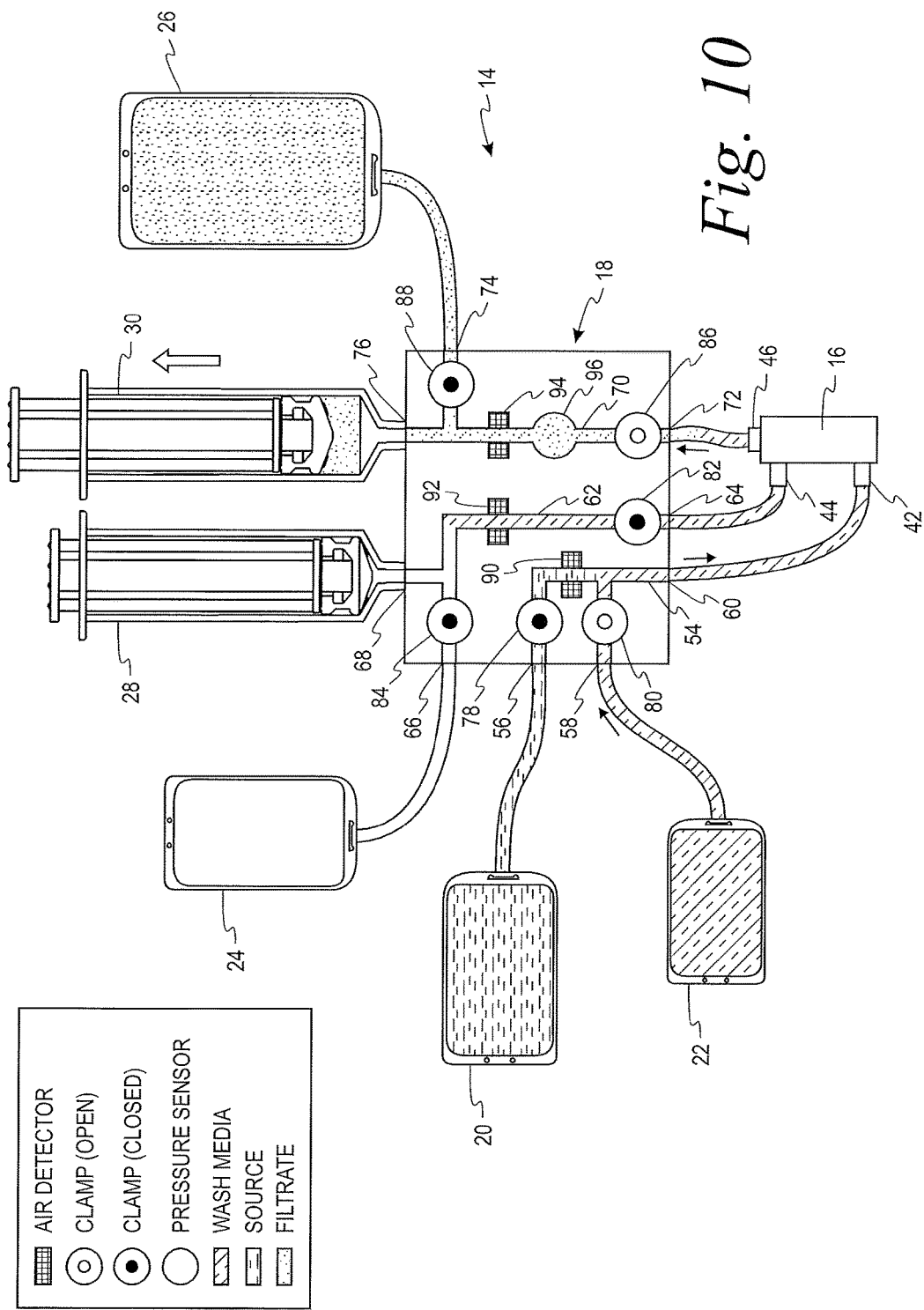
Figure 11:
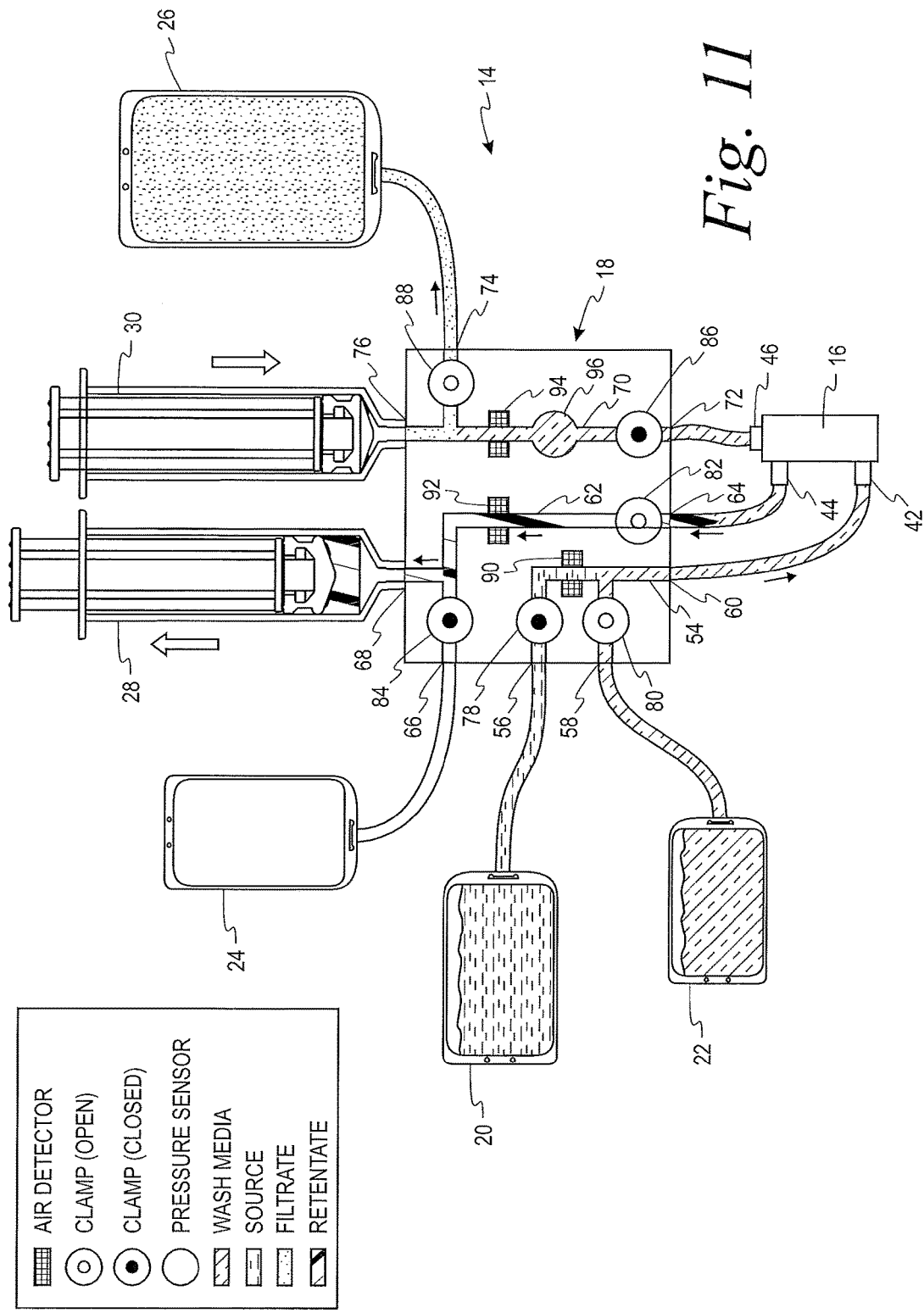

A cell washing procedure utilizing the system set forth above will now be described. The procedure includes three relatively distinct phases: a priming phase, as illustrated in FIGS. 4-6, during which the kit is primed with wash media, a loading phase, as illustrated in FIGS. 7 and 8, in which the annulus of the spinning membrane separator is filled with the cellular suspension that is to be washed, and a wash phase, as illustrated in FIGS. 9-11, in which filtrate (supernatant and wash media) and retentate (the washed cells) are drawn through the cassette and flowed to their respective containers.

Once the disposable kit 14 is loaded onto the hardware component 12, with a container 20 of the cell suspension to be washed connected to the cassette 18, the cell washing procedure may commence. As is appreciated, the procedure is automatically controlled by means of the programmable controller 40, which sequentially operates the valves/clamps and the syringe pumps, in accordance with signals received from the sensors.

The priming sequence, as illustrated, comprises three steps. In a first step, shown in FIG. 4, the first fluid flow path 54 is primed with wash media from the second inlet 58 to the valve/clamp 78 adjacent the first inlet 56 for the source container 20 to the outlet 60 connecting with the inlet 42 of the separator 16. In this step, the plunger of the first syringe 28 is withdrawn after closing valves/clamps 78, 84 and 86 and opening valves/clamps 80 and 82, thus drawing wash media out of the container 22 into the first fluid pathway 54. Wash media is drawn through the spinning membrane separator 16 and out the first outlet 44 into the second fluid pathway 62 until the sensor 92 detects an air-fluid interface, at which time the syringe pump is stopped and the plunger of the first syringe 28 no longer withdrawn. Alternatively, withdrawal (and depression) of the plunger can be controlled based on changes in volume within the barrel of the syringe that is correlated to volumes of fluid drawn through the kit. As previously noted, the disposable kit may be primed with wash media by drawing wash media from its source 22 only up to the inlet 58 to the first fluid pathway 54, to further educe the volume of wash media.

Figure 5:
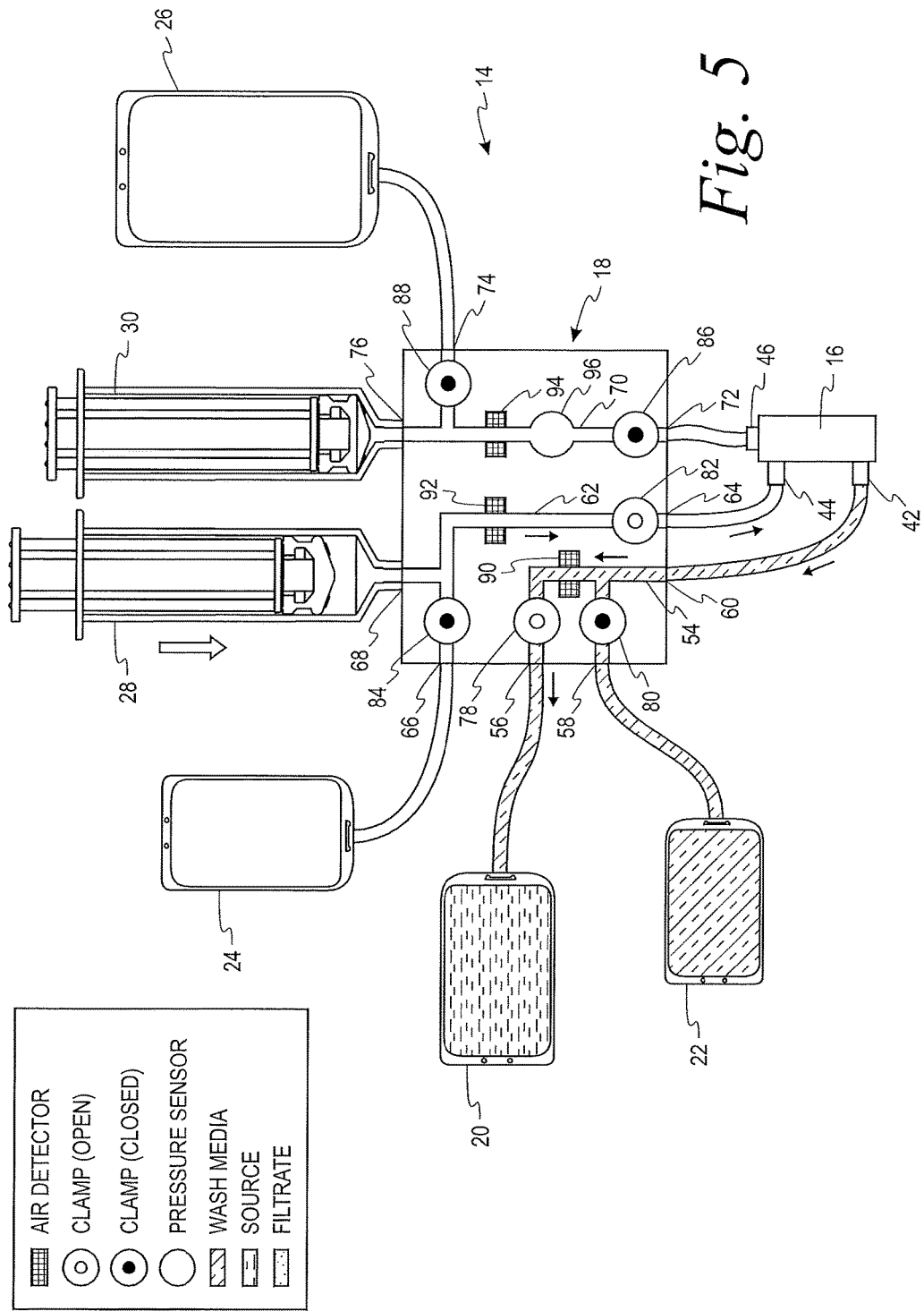

In a second step of the priming sequence, shown in FIG. 5, the plunger of the first syringe 28 is at least partially depressed, after opening valve/clamp 78 and closing valve/clamp 80, to prime the first fluid pathway 54 to the source container 20, thus completing the priming of the first fluid pathway.

In a third step of the priming sequence, shown in FIG. 6, the plunger of the first syringe 28 is completely depressed, so that no air remains in the syringe, after closing valves/clamps 78 and 82 and opening valve/clamp 84, to vent air to the retentate container 24. While not shown in the drawings, the third fluid flow path 70 may also be primed with wash media by withdrawing the plunger of the second syringe 30 after valves/clamps 78, 82 and 88 are closed and valves/clamps 80 and 86 opened, to draw wash media into the third fluid pathway. The air drawn into the second syringe 30 would then be vented into the filtrate container 26 by closing valve/clamp 86 and opening valve/clamp 88 and completely depressing the plunger.

The system is now ready for loading the annulus of the spinning membrane separator 16 with the suspension of cells to be washed. With reference to FIG. 7, this is accomplished by withdrawing the plunger of the first syringe 28 after opening valves/clamps 78 and 82 and closing valve/clamp 84. This draws cell suspension out of the source container 20 into the first fluid pathway 54 and into the spinning membrane separator 16. The wash media in the first fluid pathway 54 that resulted from priming is drawn into the second fluid pathway. The withdrawal of the plunger of the first syringe 28 is stopped when the annulus of the separator 16 is filled with cell suspension, and prior to the cell suspension reaching the second fluid pathway, as determined by, e.g., detection of an air-fluid interface by sensor 92, or upon a change in volume of the barrel of the syringe. The air drawn into the syringe 28 due to loading the separator 16 is then vented to the retentate container 24 by completely depressing the plunger of the first syringe 28 after closing the valve/clamp 82 and opening the valve/clamp 84, as shown in FIG. 8.

The supernatant is then separated from the cell suspension by the separator 16 and removed. With reference to FIG. 9, this is accomplished by withdrawing the plunger of the second syringe 30 after opening valves/clamps 78 and 86, while valves/clamps 80, 82 and 88 remain closed. As such, additional cell suspension is drawn into the separator as the supernatant flows out of the separator through outlet 46, into the third fluid flow path 70 and into the barrel of the second syringe 30, while cellular content accumulates in the annulus of the separator.

Withdrawal of the plunger of the second syringe 30 continues drawing supernatant into the barrel until the cellular content of the annulus of the separator 16 is exceeds the configured volume (based on an empirical determination of the internal volume of the spinner annulus, the rotational velocity of the spinner, the filtrate flow rate). Alternatively, the plunger of the second syringe 30 continues to draw supernatant into the barrel of the second syringe 30 until it is filled with supernatant, or the sensor 90 detects an air fluid interface, indicating that the source container 20 is empty.

The cells accumulated in the annulus of the separator 16 are then washed. With reference to FIG. 10, this is accomplished by further withdrawing the plunger of the second syringe 30 after closing valve/clamp 78 and closing valve/clamp 80, while valves/clamps 82, 84 and 88 remain closed. As such, wash media is drawn into and through the separator 16 into the second syringe 30. The plunger of the syringe continues to be withdrawn until it is either filled or container 22 is emptied of wash media.

The cells accumulated in the annulus of the separator 16 are then withdrawn to clear the annulus. With reference to FIG. 11, to this end, the plunger of the first syringe 28 is withdrawn after opening valve/clamp 82 and closing valve/clamp 86, while valves/clamps 78 and 84 are closed, thus drawing the washed cells into the barrel of the first syringe.

If the source container 20 contains additional cell suspension that is to be washed, the supernatant/wash media contained in the second syringe can be flowed into the filtrate container 26 by depressing the plunger of the second syringe after the valve/clamp 86 is closed and the valve/clamp 88 opened.

If additional cell suspension is contained in the source container 20, it can be washed by repeating the steps illustrated in FIGS. 9-11, as described above, until the container 20 is depleted. At the completion of each wash cycle, the washed cells contained in the first syringe 28 may be flowed to the retentate container 24 by fully depressing the plunger of the first syringe 28 after opening valve/clamp 84 and closing valve/clamp 82.

Figure 12:
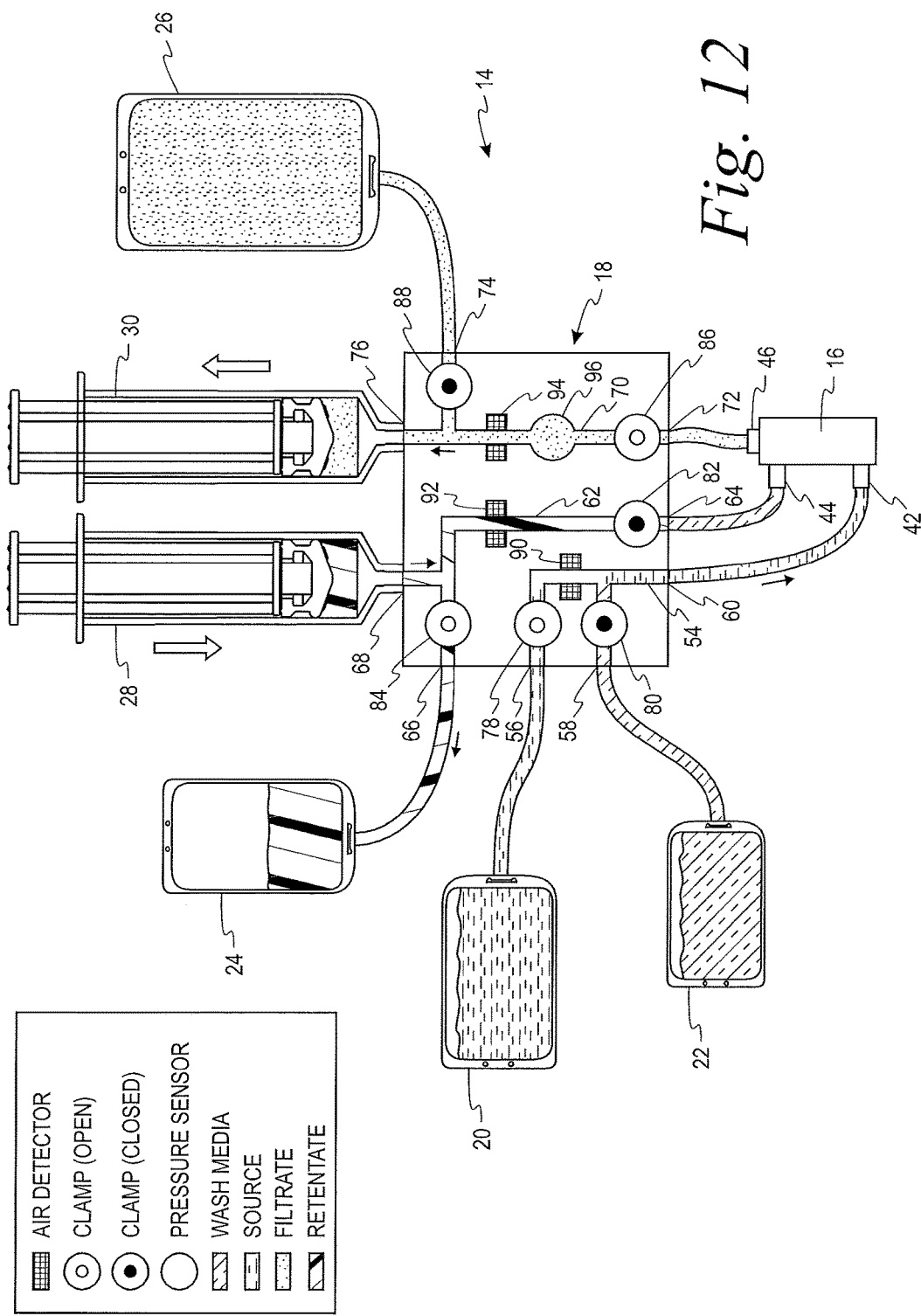

Alternatively, subsequent wash cycles may be performed as illustrated in FIGS. 12-15. Specifically, a second or subsequent volume of cell suspension is pulled from the source container 20 into the annulus of the separator 16 by closing the valves/clamps 80, 82 and 88, opening the valves/clamps 78 and 86, and withdrawing the plunger of second syringe 30 (FIG. 12). At the same time, the previous cycle's washed retentate is dumped into the retentate container 24 by opening the valve/clamp 84 and depressing the plunger of the first syringe 28.

Figure 13:
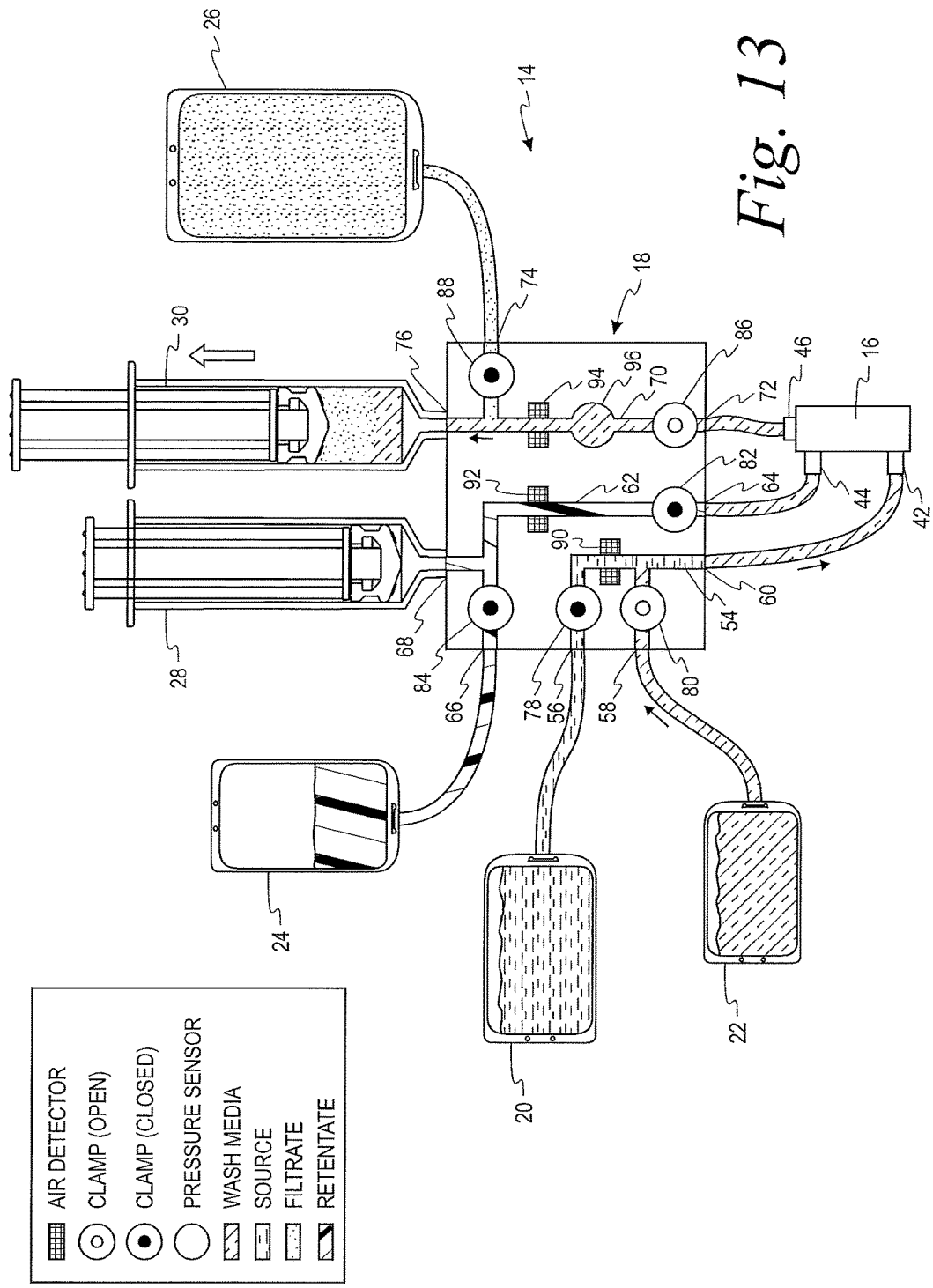

Then, with reference to FIG. 13, the supernatent in the cell suspension is removed by closing the valve/clamp 78 and opening the valve/clamp 80, so that additional wash media is drawn from the container 22 into the annulus of the spinner 16 by further withdrawing the plunger of the second syringe 30.

Figure 14:
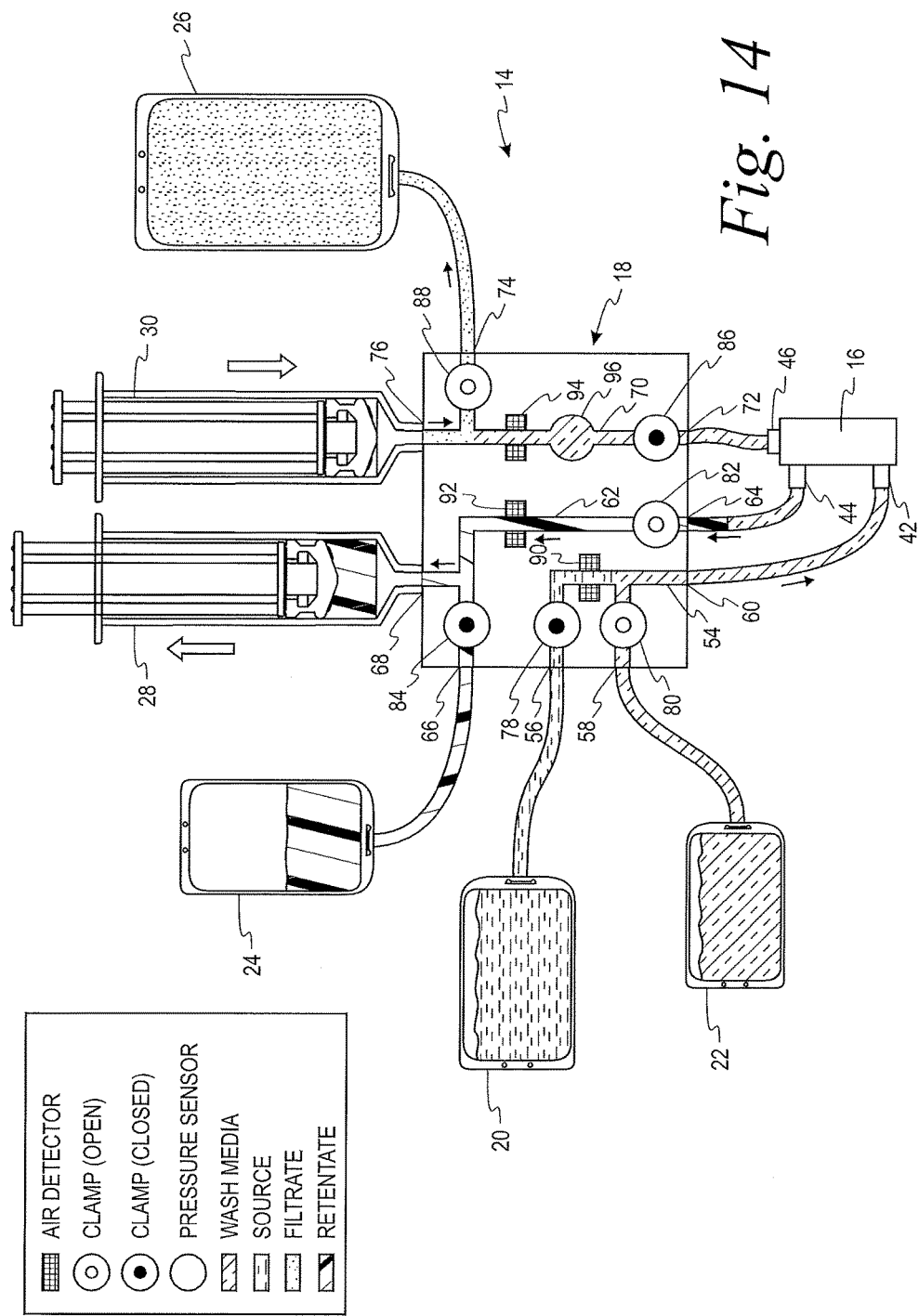

Then, the annulus of the spinner 16 is cleared by opening the valve/clamp 82 and withdrawing the plunger of the first syringe 28, thus drawing the retentate into the syringe 28 (FIG. 14). Simultaneously, the filtrate in the second syringe 30 is flowed into the filtrate container 28 by closing the valve/clamp 86 and depressing the plunger of the second syringe 30.

Figure 15:
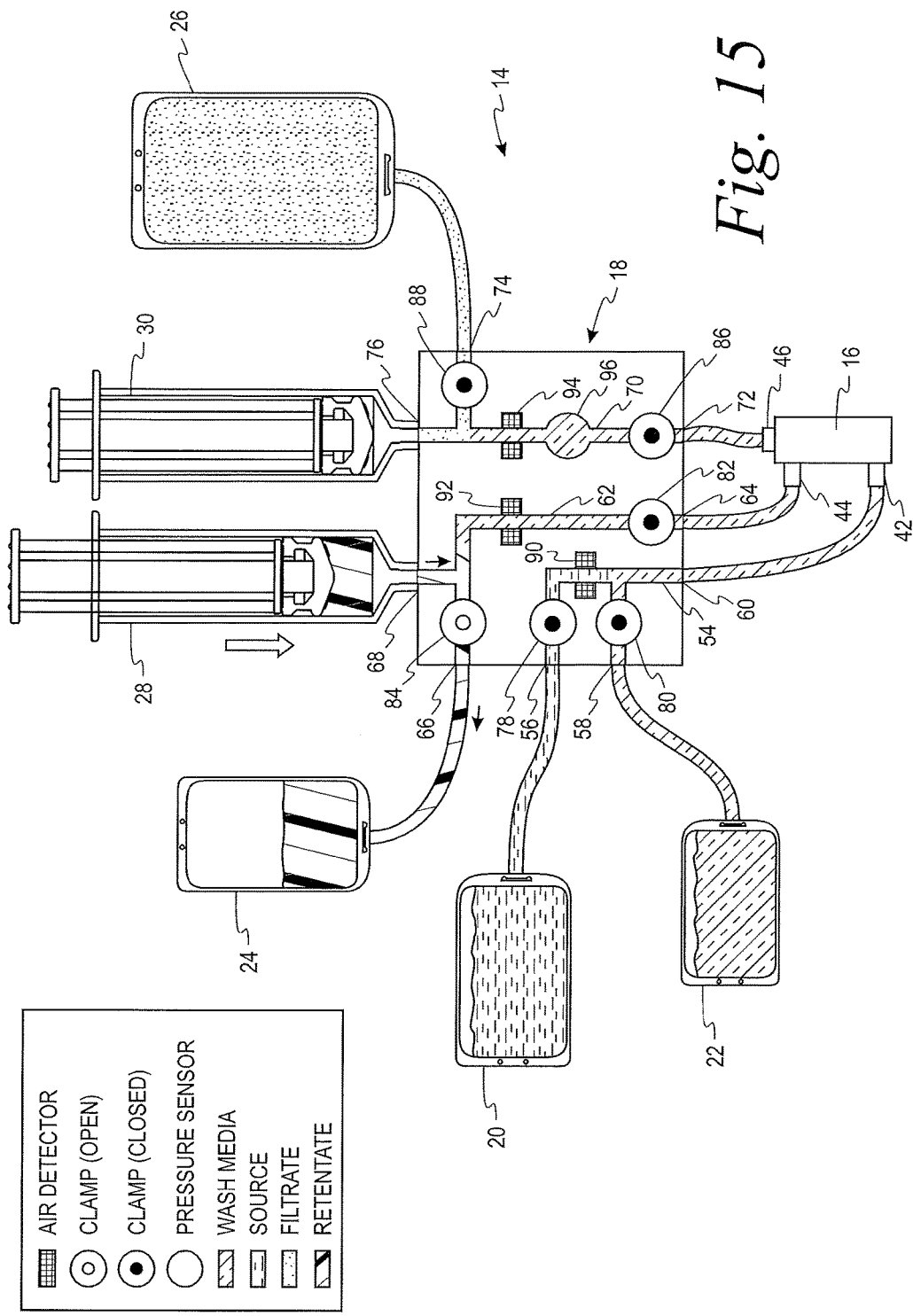

The retentate in the first syringe 28 is then flowed to the retentate container 24 by closing the valves/clamps 80, 82, opening the valve/clamp 84, and depressing the plunger of the first syringe 28, as shown in FIG. 15. The steps illustrated in FIGS. 12-15 may be repeated until the source container 20 is emptied of cell suspension.

Figure 16:
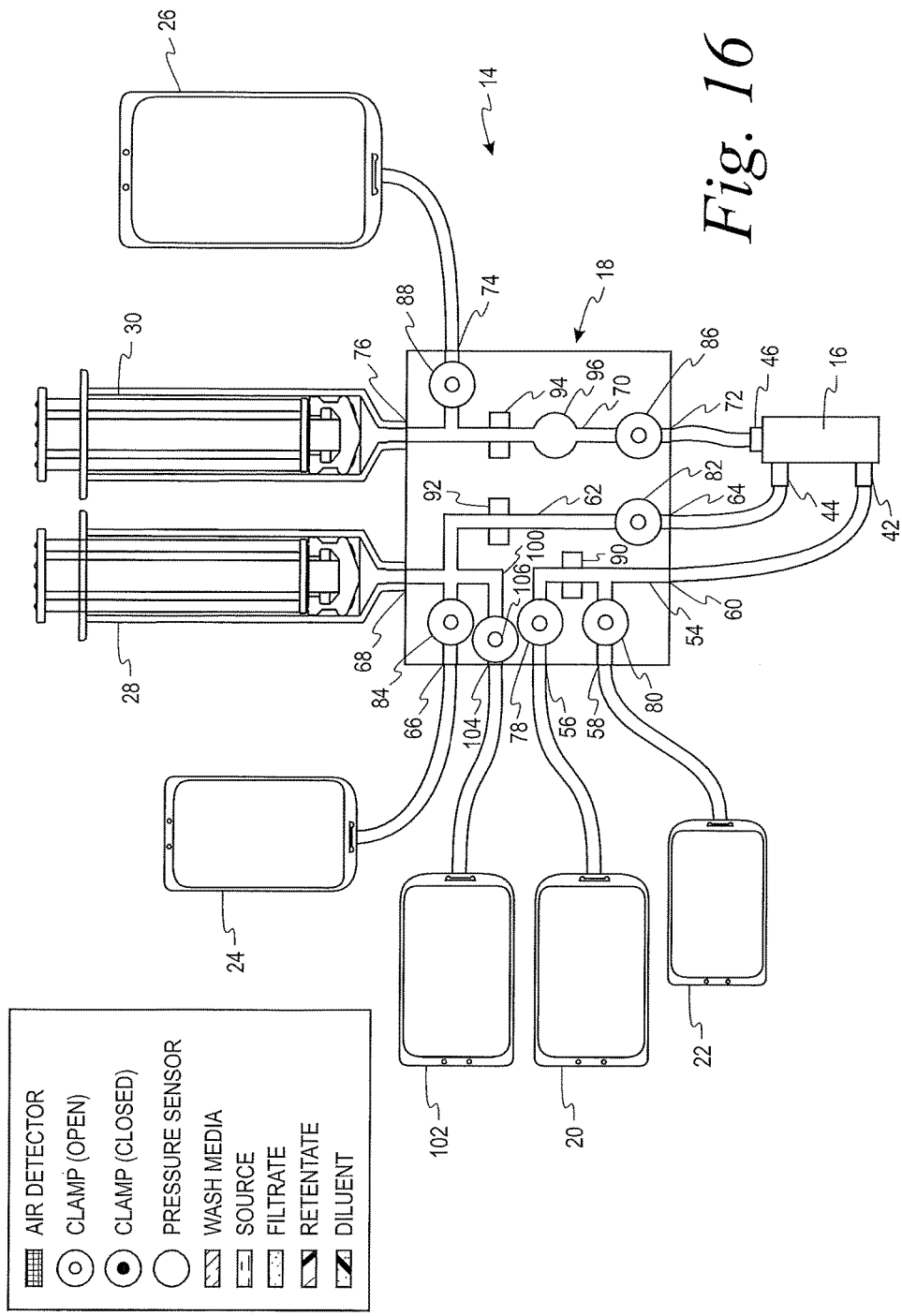
FIG. 16 is a schematic view of a second embodiment of a disposable kit for use in the system of FIG. 1 that permits the addition of a diluent to the washed cells.

Under certain circumstances, it may be desirable to dilute the washed cells comprising the retentate, for example if the retentate is to be frozen, in which case a cryoprotective agent would be used to dilute the retentate, To this end, and as illustrated in FIG. 16, the cassette 18 may be provided with a further, fourth fluid pathway 100 that provides fluid communication between the first syringe 28 and a container 102 for the diluent. The fluid pathway 100 includes an inlet 104 and a valve/clamp 106 adjacent the inlet 104 for controlling fluid flow through the pathway 100.

Figure 17:
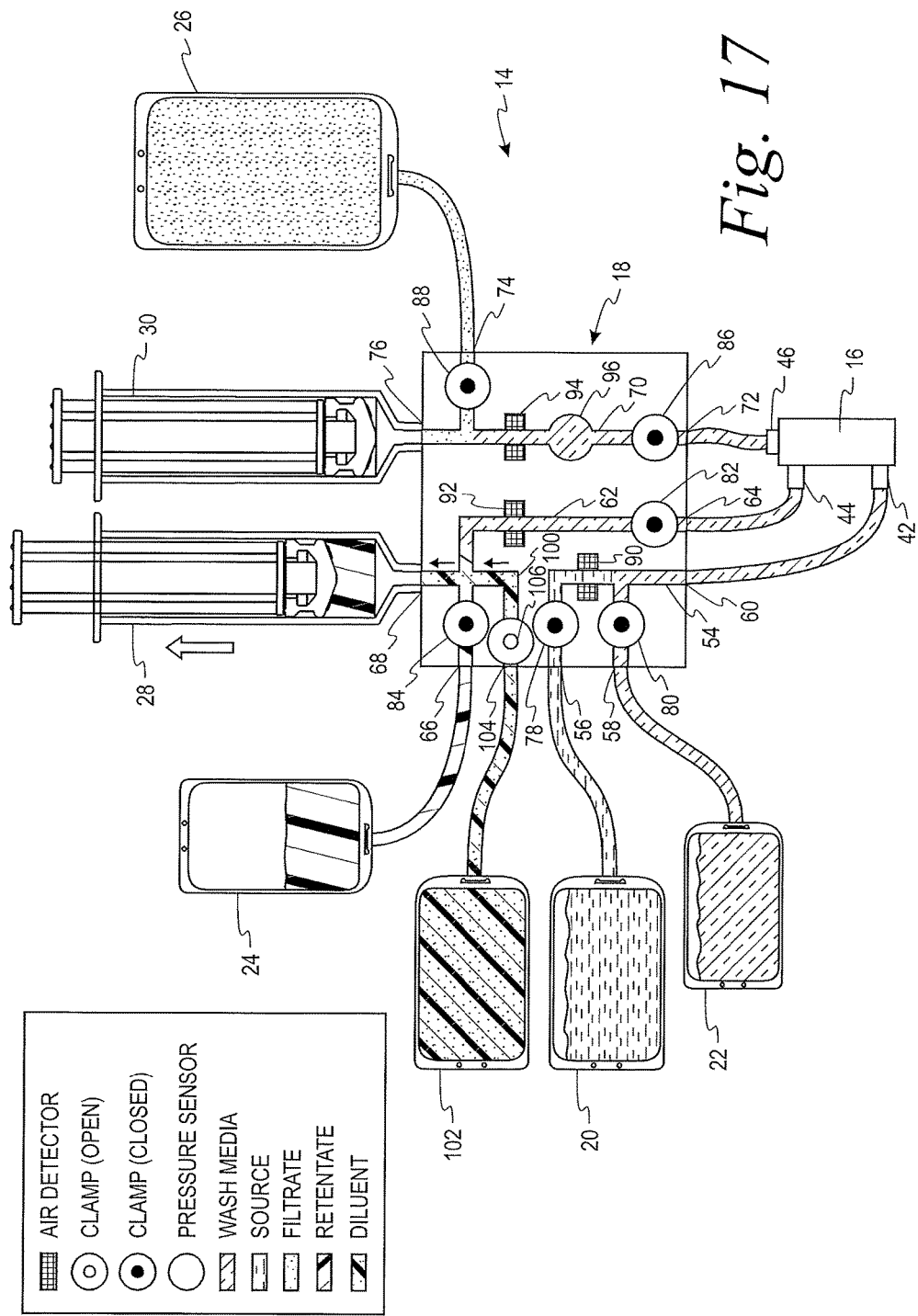
FIGS. 17 and 18 are schematic views of the disposable kit of FIG. 16 illustrating the steps of adding a diluent to the washed cells.
Figure 18:
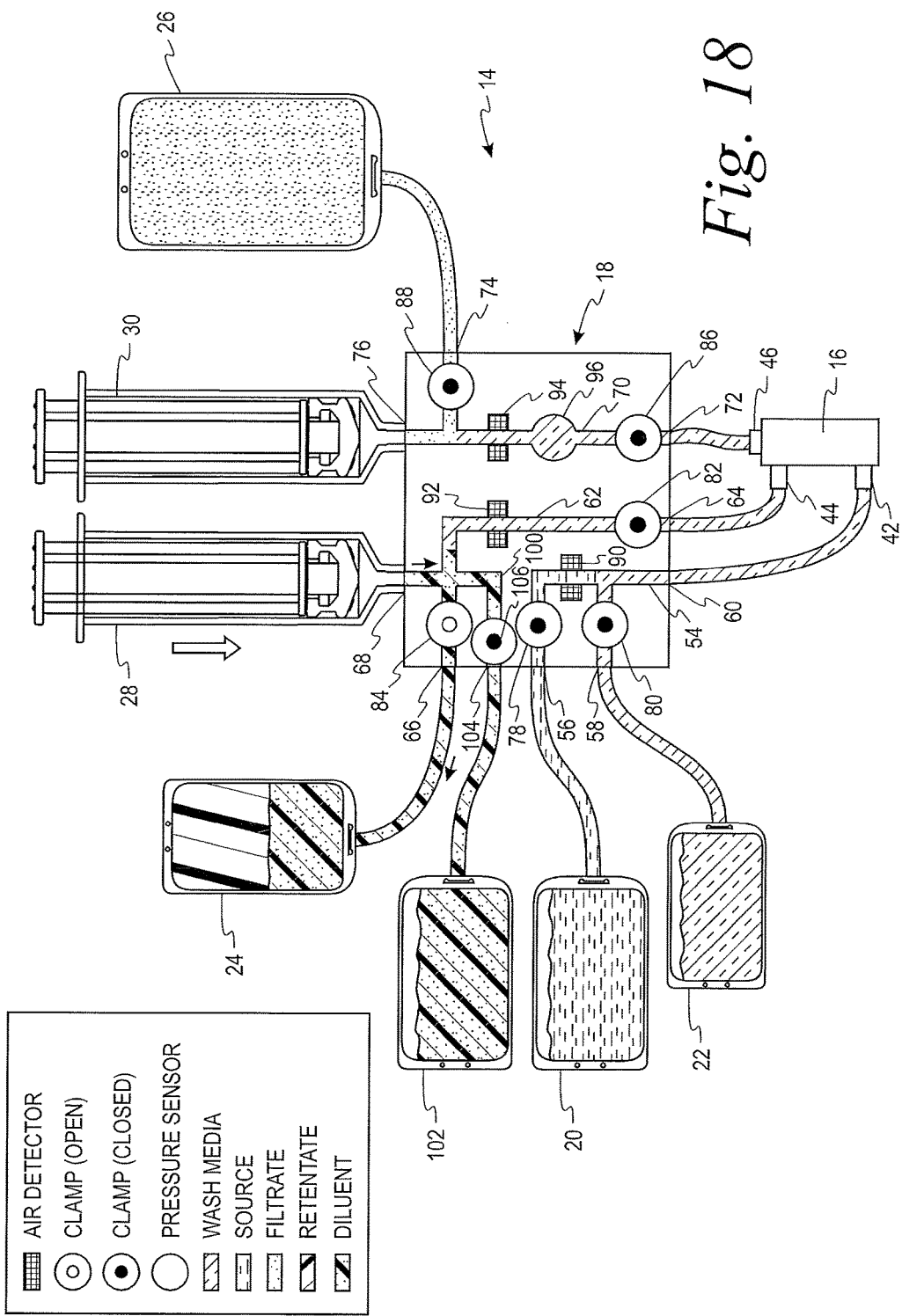

To add a diluent to the retentate in the container 24, the valves/clamps 82 and 84 are closed, while the valve/clamp 106 is opened. The plunger of the first syringe 28 is withdrawn to flow diluent out of the container 102 and into the syringe 28 (as shown in FIG. 17. Then, the valve/clamp 106 is closed and the valve/clamp 84 opened. The plunger of the first syringe 28 is then depressed to flow diluent into container 24 (as shown in FIG. 18).

Thus, an improved method and system for washing small volumes of biological cells has been disclosed. The description provided above is intended for illustrative purposes, and is not intended to limit the scope of the disclosure to any particular method, system, apparatus or device described herein.

The invention claimed is:

1. A disposable kit for washing a suspension of cellular material containing target and non-target components comprising:
   a) a spinning membrane separator having an inlet for flowing the suspension of cellular material to be washed and a wash medium into the spinning membrane separator, a first outlet for flowing retentate comprising a target component from the spinning membrane separator, and a second outlet for flowing filtrate comprising a non-target component of the cellular suspension and wash medium from the spinning membrane separator;
   b) a first container for receiving the retentate;
   c) a second container for receiving the filtrate;
   d) a third container of the wash medium;
   e) a first syringe comprising a barrel with a discharge port and a plunger;
   f) a second syringe comprising a barrel with a discharge port and a plunger; and
   g) a flow control cassette comprising a housing and having a first fluid pathway with a first inlet configured to be in fluid communication with a source of the suspension of cellular material to be washed, a second inlet configured to be in fluid communication with the third container of wash medium, and an outlet in fluid communication with the inlet of the spinning membrane separator; a second fluid pathway with an inlet in fluid communication with the first outlet of the spinning membrane separator for flowing retentate, a first outlet in fluid communication with the first container for receiving the retentate, and a second outlet in fluid communication with the first syringe; a third fluid pathway with an inlet in fluid communication with the second outlet of the spinning membrane separator for flowing filtrate, a first outlet in fluid communication with the second container for receiving the filtrate, and a second outlet in fluid communication with the second syringe; at least one valve or clamp located internal to the cassette for selectively occluding the fluid pathways associated with each of the first, second and third fluid pathways; and at least one fluid interface detector located internal to the cassette associated with each of the first, second and third fluid pathways.

2. The disposable kit of claim 1 wherein a valve or clamp is associated with each of the first inlet and second inlet of the first fluid pathway, the inlet and first outlet of the second fluid flow pathway, and the inlet and first outlet of the third fluid pathway.

3. The disposable kit of claim 1 wherein the second fluid pathway of the flow control cassette further comprises a second inlet configured to be in fluid communication with a source of diluent, and a valve or clamp located internal to the cassette is associated with the second inlet of the second fluid pathway.

4. The disposable kit of claim 1 wherein each of the first and second syringes is removably secured directly to the housing of the cassette by the discharge port.

5. The disposable kit of claim 1 wherein the barrel of each of the first and second syringes is formed integrally with the housing of the flow control cassette.

6. The disposable kit of claim 1 wherein the separator is located within the housing of the flow control cassette.

7. A method for washing a suspension of cells comprising:
 mounting to a reusable hardware component a disposable kit comprising:
  a) a spinning membrane separator having an inlet for flowing the suspension of cellular material to be washed and a wash medium into the spinning membrane separator, a first outlet for flowing retentate comprising a target component from the spinning membrane separator, and a second outlet for flowing filtrate comprising a non-target component of the cellular suspension and wash media from the spinning membrane separator;
  b) a first container for receiving the retentate;
  c) a second container for receiving the filtrate;
  d) a third container of the wash media;
  e) a first syringe comprising a barrel with a discharge port and a plunger;
  f) a second syringe comprising a barrel with a discharge port and a plunger; and
  g) a flow control cassette comprising a housing and having a first fluid pathway with a first inlet configured to be in fluid communication with a source of the suspension of cellular material to be washed, a second inlet configured to be in fluid communication with the third container of wash media, and an outlet in fluid communication with the inlet of the spinning membrane separator; a second fluid pathway with an inlet in fluid communication with the first outlet of the spinning membrane separator for flowing retentate, a first outlet in fluid communication with the first container for receiving the retentate, and a second outlet in fluid communication with the first syringe; a third fluid pathway with an inlet in fluid communication with the second outlet of the spinning membrane separator for flowing filtrate, a first outlet in fluid communication with the second container for receiving the filtrate, and a second outlet in fluid communication with the second syringe; at least one valve or clamp located internal to the cassette for selectively occluding the fluid pathways associated with each of the first, second and third fluid pathways; and at least one fluid interface detector located internal to the cassette associated with each of the first, second and third fluid pathways;
 priming the disposable kit with wash media;
 loading the spinning membrane separator with a volume of cellular material to be washed;
 washing the cellular material by introducing wash media to the spinning membrane separator to remove supernatant and non-target materials from the spinning membrane separator;
 clearing the spinning membrane separator of washed cells; and
 flowing the washed cells to the container for receiving retentate; wherein the priming, loading, washing, clearing and flowing steps are controlled by a programmable controller based on signals received from the fluid interface detectors associated with each of the first, second and third fluid pathways.

8. The method of claim 7 wherein the disposable kit is primed with wash media from the third container by withdrawing the plunger of the first syringe while occluding the first fluid pathway adjacent its first inlet, the second fluid pathway adjacent its first outlet, and the third pathway adjacent its inlet to draw wash media into the first fluid pathway; at least partially depressing the plunger of the first syringe while opening the first fluid pathway adjacent its first outlet and occluding the first fluid pathway adjacent its second inlet to prime the first fluid pathway up to the source of the suspension of cellular material to be washed; and further depressing the plunger of the first syringe while opening the second fluid pathway adjacent its first outlet and occluding the first fluid pathway adjacent its inlet to vent air to the first container for receiving retentate.

9. The method of claim 8 wherein the spinning membrane separator is loaded with a volume of the suspension of cellular material to be washed by withdrawing the plunger of the first syringe while opening the first fluid pathway adjacent its first inlet and occluding the first fluid pathway adjacent its second inlet, opening the second fluid pathway adjacent its inlet and occluding the second fluid flow path adjacent its first outlet; and occluding the third fluid pathway adjacent its inlet to draw the volume of suspension into the separator; and depressing the plunger of the first syringe while opening the second fluid pathway adjacent its first outlet and occluding the first fluid pathway adjacent its inlet to vent air to the first container for receiving the retentate.

10. The method of claim 9 wherein the volume of the suspension of cells in the separator is washed by withdrawing the plunger of the second syringe while opening the first fluid pathway adjacent its first inlet and occluding the first fluid pathway adjacent its second inlet, occluding the second fluid pathway adjacent its inlet, and opening the third fluid path way adjacent its inlet and occluding the third fluid flow path adjacent its first outlet to simultaneously draw additional suspension into the separator and supernatant into the second syringe; further withdrawing the plunger of the second syringe while occluding the first fluid pathway adjacent its first inlet and opening the first fluid pathway adjacent its second inlet, occluding the second fluid pathway adjacent its inlet, and occluding the third fluid pathway adjacent its first outlet to draw wash media into and through the spinning membrane separator and into the second syringe.

11. The method of claim 10 wherein the spinning membrane separator is cleared of washed cells by occluding the third fluid pathway adjacent its inlet and opening the third fluid pathway adjacent its first outlet while depressing the plunger of the second syringe to flow supernatant and wash media into the second container for receiving the filtrate, and opening the second fluid pathway adjacent its inlet and occluding the second fluid pathway adjacent its first outlet, occluding the first fluid pathway adjacent its first inlet and opening the first fluid pathway adjacent its second inlet while withdrawing the plunger of the first syringe to draw washed cellular matter into the first syringe.

12. The method of claim 11 further comprising flowing washed cellular material from the first syringe to the first container for receiving the retentate by depressing the plunger of the first syringe while occluding the second fluid pathway adjacent its inlet and opening the second fluid pathway adjacent its first outlet.

13. The method of claim 11 further comprising repeating the steps of loading the spinning membrane separator, washing the volume of cells in the separator, and clearing the spinning membrane of washed cells until the source of the suspension of cellular material to be washed is emptied.

14. The method of claim 7 further comprising introducing a diluent into the first container for receiving the retentate after the washed cellular material has been received therein.

15. The method of claim 14 further comprising occluding the second fluid pathway adjacent the first outlet and opening the second fluid pathway adjacent the second inlet; withdrawing the plunger of the first syringe to draw diluent into the first syringe; opening the second fluid pathway adjacent the first outlet and occluding the second fluid pathway adjacent the second inlet, and depressing the plunger of the first syringe to flow diluent through the first outlet of the second fluid pathway and into the first container for receiving the retentate.

16. The method of claim 7 wherein the washed cells have a final volume of less than 50 mL.

17. The method of claim 7 wherein the washed cells have a final volume of 10 mL.

* * * * *